US009498114B2

(12) United States Patent
Friedman et al.

(10) Patent No.: US 9,498,114 B2
(45) Date of Patent: Nov. 22, 2016

(54) SYSTEMS AND METHODS FOR DETERMINING BIOMECHANICAL PROPERTIES OF THE EYE FOR APPLYING TREATMENT

(71) Applicant: Avedro, Inc., Waltham, MA (US)

(72) Inventors: Marc D. Friedman, Needham, MA (US); David Muller, Boston, MA (US); Amit Paranjape, Waltham, MA (US)

(73) Assignee: Avedro, Inc., Waltham, MA (US)

( * ) Notice: Subject to any disclaimer, the term of this patent is extended or adjusted under 35 U.S.C. 154(b) by 327 days.

(21) Appl. No.: 14/335,372

(22) Filed: Jul. 18, 2014

(65) Prior Publication Data

US 2014/0368793 A1 Dec. 18, 2014

Related U.S. Application Data

(63) Continuation-in-part of application No. 14/308,678, filed on Jun. 18, 2014.
(Continued)

(51) Int. Cl.
*A61B 3/14* (2006.01)
*A61B 3/00* (2006.01)
(Continued)

(52) U.S. Cl.
CPC .............. *A61B 3/0025* (2013.01); *A61B 3/10* (2013.01); *A61B 3/107* (2013.01); *A61B 3/1025* (2013.01);
(Continued)

(58) Field of Classification Search
CPC ................ A61B 3/0025; A61B 3/1025; A61B 3/14; A61B 3/152; A61B 3/10; A61B
(Continued)

(56) References Cited

U.S. PATENT DOCUMENTS 4,034,750 A 7/1977 Seiderman
4,161,013 A 7/1979 Grodzinsky et al.
(Continued)

FOREIGN PATENT DOCUMENTS

DE 10 2008 046834 3/2010
EP 1 561 440 8/2005
(Continued)

OTHER PUBLICATIONS

Acosta A. et al., "Corneal Stroma Regeneration in Felines After Supradescemetic Keratoprothesis Implantation," *Cornea*, vol. 25, No. 7, pp. 830-838; Aug. 2006 (9 pages).
(Continued)

*Primary Examiner* — Bumsuk Won
*Assistant Examiner* — Collin X Beatty
(74) *Attorney, Agent, or Firm* — McDonnell Boehnen Hulbert & Berghoff LLP

(57) ABSTRACT

A system for determining biomechanical properties of corneal tissue includes a light source configured to provide an incident light and a confocal microscopy system configured to scan the incident light across a plurality of cross-sections of corneal tissue. The incident light is reflected by the corneal tissue as scattered light. The system also includes a filter or attenuating device configured to block or attenuate the Rayleigh peak frequency of the scattered light, a spectrometer configured to receive the scattered light and process frequency characteristics of the received scattered light to determine a Brillouin frequency shift in response to the Rayleigh peak frequency being blocked or attenuated by the filter or attenuating device, and a processor configured to determine a three-dimensional profile of the corneal tissue according to the determined Brillouin frequency shift. The three-dimensional profile provides an indicator of one or more biomechanical properties of the corneal tissue.

30 Claims, 8 Drawing Sheets

Related U.S. Application Data

(60) Provisional application No. 61/864,087, filed on Aug. 9, 2013, provisional application No. 61/856,244, filed on Jul. 19, 2013, provisional application No. 61/836,211, filed on Jun. 18, 2013, provisional application No. 61/836,221, filed on Jun. 18, 2013.

(51) Int. Cl.
*A61B 3/10* (2006.01)
*G02B 27/00* (2006.01)
*G01J 3/44* (2006.01)
*A61B 3/107* (2006.01)
*A61B 3/15* (2006.01)
*A61B 5/00* (2006.01)

(52) U.S. Cl.
CPC ............... *A61B 3/14* (2013.01); *G01J 3/4412* (2013.01); *G02B 27/0093* (2013.01); *A61B 3/152* (2013.01); *A61B 5/0075* (2013.01)

(58) Field of Classification Search
CPC ............ 3/107;A61B 3/101; A61B 3/102; A61B 3/113; A61B 3/12; A61B 3/1225; A61B 3/145; A61B 5/0073; A61B 5/0075; G01J 3/4412; G02B 27/0093
USPC ....... 351/204, 205, 206, 208, 209, 210, 212, 351/215, 221, 246, 247; 600/425; 606/4
See application file for complete search history.

(56) References Cited

U.S. PATENT DOCUMENTS

| | | |
|---|---|---|
| 4,326,529 A | 4/1982 | Doss et al. |
| 4,381,007 A | 4/1983 | Doss |
| 4,665,913 A | 5/1987 | L'Esperance, Jr. et al. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0041856 A1 | 11/2001 | Mcdaniel |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0189689 A1 | 10/2003 | Rathjen |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly et al. |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |

(56) References Cited

U.S. PATENT DOCUMENTS

| | | |
|---|---|---|
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey |
| 2010/0094197 A1 | 4/2010 | Marshall et al. |
| 2010/0114109 A1 | 5/2010 | Peyman |
| 2010/0149487 A1 | 6/2010 | Ribak |
| 2010/0149842 A1 | 6/2010 | Muller et al. |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Ornberg et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | De Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0203051 A1 | 8/2012 | Brooks et al. |
| 2012/0203161 A1 | 8/2012 | Herekar |
| 2012/0215155 A1 | 8/2012 | Muller et al. |
| 2012/0283621 A1 | 11/2012 | Muller et al. |
| 2012/0289886 A1 | 11/2012 | Muller et al. |
| 2012/0302862 A1* | 11/2012 | Yun ..................... A61B 5/0075 600/398 |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0194957 A1 | 7/2014 | Rubinfeld et al. |
| 2014/0249509 A1 | 9/2014 | Rubinfeld et al. |

FOREIGN PATENT DOCUMENTS

| | | |
|---|---|---|
| EP | 1 790 383 | 5/2007 |
| EP | 2 253 321 | 11/2010 |
| EP | 2 490 621 | 8/2012 |
| IT | MI2010A001236 | 5/2010 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | WO 00/74648 | 12/2000 |
| WO | WO 01/58495 | 8/2001 |
| WO | WO 2004/052223 | 6/2004 |
| WO | WO 2005/110397 | 11/2005 |
| WO | WO 2006/012947 | 2/2006 |
| WO | WO 2006/128038 | 11/2006 |
| WO | WO 2007/001926 | 1/2007 |
| WO | WO 2007/053826 | 5/2007 |
| WO | WO 2007/081750 | 7/2007 |
| WO | WO 2007/120457 | 10/2007 |
| WO | WO 2007/139927 | 12/2007 |
| WO | WO 2007/143111 | 12/2007 |
| WO | WO 2008/000478 | 1/2008 |
| WO | WO 2008/052081 | 5/2008 |
| WO | WO 2008/095075 | 8/2008 |
| WO | WO 2009/073213 | 6/2009 |
| WO | WO 2009/114513 | 9/2009 |
| WO | WO 2009/146151 | 12/2009 |
| WO | WO 2010/011119 | 1/2010 |
| WO | WO 2010/015255 | 2/2010 |
| WO | WO 2010/023705 | 3/2010 |
| WO | WO 2010/093908 | 8/2010 |
| WO | WO 2011/019940 | 2/2011 |
| WO | WO 2011/116306 | 9/2011 |
| WO | WO 2012/004726 | 1/2012 |
| WO | WO 2012/047307 | 4/2012 |
| WO | WO 2012/149570 | 11/2012 |
| WO | WO 2012/174453 | 12/2012 |
| WO | WO 2013/148713 | 10/2013 |
| WO | WO 2013/148895 | 10/2013 |
| WO | WO 2013/148896 | 10/2013 |
| WO | WO 2013/149075 | 10/2013 |
| WO | WO 2014/202736 | 12/2014 |

OTHER PUBLICATIONS

Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html (3 pages).

Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).

Berjano E., et al., "Radio-Frequency Heating of the Cornea: Theoretical Model and *In Vitro* Experiments," *IEEE Transactions on Biomedical Engineering*, vol. 49, No. 3, pp. 196-205; Mar. 2002 (10 pages).

Berjano E., et al., "Ring Electrode for Radio-frequency Heating of the Cornea: Modelling and *in vitro* Experiments," *Medical & Biological Engineering & Computing*, vol. 41, pp. 630-639; Jun. 2003 (10 pages).

Brüel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

(56) References Cited

OTHER PUBLICATIONS

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).
Chandonnet, "$CO_2$ Laser Annular Thermokeratoplasty: A Preliminary Study," *Lasers in Surgery and Medicine*, vol. 12, pp. 264-273; 1992 (10 pages).
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).
Corbett M., et al., "Effect of Collagenase Inhibitors on Corneal Haze after PRK," *Exp. Eye Res.*, vol. 72, Issue 3, pp. 253-259; Jan. 2001 (7 pages).
Coskenseven E. et al., "Comparative Study of Corneal Collagen Cross-linking With Riboflavin and UVA Irradiation in Patients With Keratoconus," *Journal of Refractive Surgery*, vol. 25, issue 4, pp. 371-376; Apr. 2009 (6 pages).
"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).
Ehlers W., et al., "Factors Affecting Therapeutic Concentration of Topical Aminocaproic Acid in Traumatic Hyphema," *Investigative Ophthalmology & Visual Science*, vol. 31, No. 11, pp. 2389-2394; Nov. 1990 (6 pages).
Erskine H., "Avedro Becomes Sponsor of US FDA Clinical Trials of Corneal Collagen Crosslinking," Press Release, Mar. 16, 2010 (1 page).
Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011 (10 pages).
Frucht-Pery, et al. "Iontophoresis—gentamicin delivery into the rabbit cornea, using a hydrogel delivery probe, " Jun. 20, 2003 (5 pages).
Gibson, Q. et al., "The Oxidation of Reduced Flavin Mononucleotide by Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al. "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).
Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).
Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).
Hitzenberger et al., "Birefringence Properties of the Human Cornea Measured With Polarization Sensitive Optical Coherence Tomography," Bull. Soc. Beige Ophtalmol., 302, 153-168, 2006 (16 pages).
Holmström, B. et al., "Riboflavin As an Electron Donor in Photochemical Reactions," 1867-1871, Nov. 29, 1960 (5 pages).
How to Use DEFINITY: "Frequently Asked Questions;" retrieved from http://www.definityimaging.com/how-faq.html, on Sep. 26, 2011 (3 pages) (date unknown, prior to Apr. 26, 2010).

IMEX, "KXL System: Crosslinking Para Cirugia Corneal Bibliografia Cientifica," Product Literature, Nov. 23, 2010 (24 pages).
Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," *Investigative Ophthalmology & Visual Science*, vol. 51, No. 8, pp. 3929-3934; Aug. 2010 (6 pages).
Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).
Koller, T. et. Al., "Complication and failure rates after corneal crosslinking," *Journal Cataract and refractive surgery*, vol. 35, No. 8, Aug. 2009, pp. 1358-1362.
Koller T., et al., "Therapeutische Quervernetzung der Hornhaut mittels UVA and Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).
Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).
Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Marzouky, et. al., Tensioactive-mediated Transepithelial Corneal Cross-linking—First Laboratory Report, European Ophthalmic Review, 2009, 3(2), pp. 67-70.
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Mi S., et al., "The adhesion of Lasik-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," *Br. J. Opthalmol.*, vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism,"*J. Cataract Refract. Surg.*, vol. 32(5), pp. 732-741; May 2006 (10 pages).
Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
O.V. Shilenskaya et al., "Vtorichnaya katarakta posle implantatsii myagkikh IOL," [online] Aug. 21, 2008 [retrieved Apr. 3, 2013] Retrieved from the Internet: <URL:http://www.reper.ru/rus/index.php?catid=210> (4 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

(56) References Cited

OTHER PUBLICATIONS

Pallikaris I., et al., "Long-term Results of Conductive Keratoplasty for low to Moderate Hyperopia,"*J. Cataract Refract. Surg.*, vol. 31(8), pp. 1520-1529; Aug. 2005 (10 pages).
Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).
Pinelli R., et al., "C3-Riboflavin Treatments: Where Did We Come From? Where Are We Now?" *Cataract & Refractive Surgery Today Europe*, Summer 2007, pp. 36-46; Jun. 2007 (10 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).
Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Rocha K., et al., "Comparative Study of Riboflavin-UVA Cross-linking and "Flash-linking" Using Surface Wave Elastometry," *Journal of Refractive Surgery*, vol. 24 Issue 7, pp. S748-S751; Sep. 2008 (4 pages).
Rolandi et al., "Correlation of Collagen-Linked Fluorescence and Tendon Fiber Breaking Time." Gerontology 1991;27:240-243 (4 pages).
RxList: "Definity Drug Description;" *The Internet Drug Index*, revised Jun. 16, 2008, retrieved from http://www.rxlist.com/definity-drug.htm, on Sep. 26, 2011 (4 pages).
Sheehan M., et al., "Illumination System for Corneal Collagen Crosslinking," *Optometry and Vision Science*, vol. 88, No. 4, pp. 512-524; Apr. 2011 (13 pages).
Shell, J., "Pharmacokinetics of Topically Applied Ophthalmic Drugs," *Survey of Ophthalmology*, vol. 26, No. 4, pp. 207-218; Jan.-Feb. 1982 (12 pages).
Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).
Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).
Spoerl E., et al., "Artificial Stiffening of the Cornea by Induction of Intrastromal Cross-links," *Der Ophthalmologe*, vol. 94, No. 12, pp. 902-906; Dec. 1997 (5 pages).
Spoerl E., et al., "Induction of Cross-links in Corneal Tissue," *Experimental Eye Research*, vol. 66, Issue 1, pp. 97-103; Jan. 1998 (7 pages).
Spoerl E. et al., "Safety of UVA-Riboflavin Cross-Linking of the Cornea," *Cornea*, vol. 26, No. 4, pp. 385-389; May 2007 (5 pages).
Spoerl E., et al., "Techniques for Stiffening the Cornea," *Journal of Refractive Surgery*, vol. 15, Issue 6, pp. 711-713; Nov.-Dec. 1999 (4 pages).
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thornton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.

Trembly et al., "Microwave Thermal Keratoplasty for Myopia: Keratoscopic Evaluation in Porcine Eyes," *Journal of Refractive Surgery*, vol. 17, No. 6, pp. 682-688; Nov./Dec. 2001 (8 pages).
"UV-X: Radiation System for Treatment of Keratokonus," *PESCHKE Meditrade GmbH*; retrieved from http://www.peschkemed.ch/ on Sep. 27, 2011 (date unknown, prior to Sep. 16, 2008) (1 page).
Vasan S., et al., "An agent cleaving glucose-derived protein crosslinks in vitro and in vivo;" *Letters to Nature*, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).
Wollensak G., et al., "Collagen Crosslinking of Human and Porcine Sclera," *J. Cataract Refract. Surg.*, vol. 30, Issue 3, pp. 689-695; Mar. 2004 (7 pages).
Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).
Wollensak G., "Crosslinking Treatment of Progressive Keratoconus: New Hope," *Current Opinion in Ophthalmology*, vol. 17(4), pp. 356-360; Aug. 2006 (5 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970) (5 pages).
Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.
Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 15, 2011 (pp. 13011-13022).
Zderic V., et al., "Drug Delivery Into the Eye With the Use of Ultrasound," *J. Ultrasound Med*, vol. 23(10), pp. 1349-1359; Oct. 2004 (11 pages).
Zderic V., et al., "Ultrasound-enhanced Transcorneal Drug Delivery," *Cornea* vol. 23, No. 8, pp. 804-811; Nov. 2004 (8 pages).
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Barbarino, S. et al., "Post-LASIK ectasia: Stabilization and Effective Management with Riboflavin / ultraviolet A-induced collagen cross-linking," Association for Research in Vision and Ophthalmology, 2006 (1 page).
Burke, JM et al., Abstract for "Retinal proliferation in response to vitreous hemoglobin or iron", Investigative Ophthalmology & Visual Science, May 1981, 20(5), pp. 582-92 (1 page).

(56) References Cited

OTHER PUBLICATIONS

Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480 (1 page).
Friedman, M. et al. "Advanced Corneal Cross-Linking System with Fluorescence Dosimetry", Journal of Ophthalmology, vol. 2012, Article ID 303459, dated May 7, 2012 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Meek, K.M. et al. "The Cornea and Scleera", Collagen: Structure and Mechanics, Chapter 13, pp. 359-396, 2008 (38 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli R., "The Italian Refractive Surgery Society (SICR) results using C3-R" presented Jun. 22-23, 2007 in Italy (13 pages).
Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Turgunbaev N.A. et al. Fotomodifikatsiya sklery u bolnykh s progressiruyuschei blizorukostyu (predvaritelnoe soobschenie). 2010 [online]. Retrieved from the Internet:<URL:http://www.eyepress.ru/article.aspx?7484> (2 pages).
Wong, J. et al., "Post-Lasik ectasia: PRK following previous stablization and effective management with Riboflavin / ultraviolet A-induced collagen cross-linking," Association for Research in Vision and Ophthalmology, 2006 (1 page).
International Search Report and Written Opinion for PCT/US2014/043052, mailed Oct. 13, 2014 (14 pages).
International Search Report and Written Opinion for PCT/US2014/047244, mailed Nov. 6, 2014 (6 pages).

\* cited by examiner

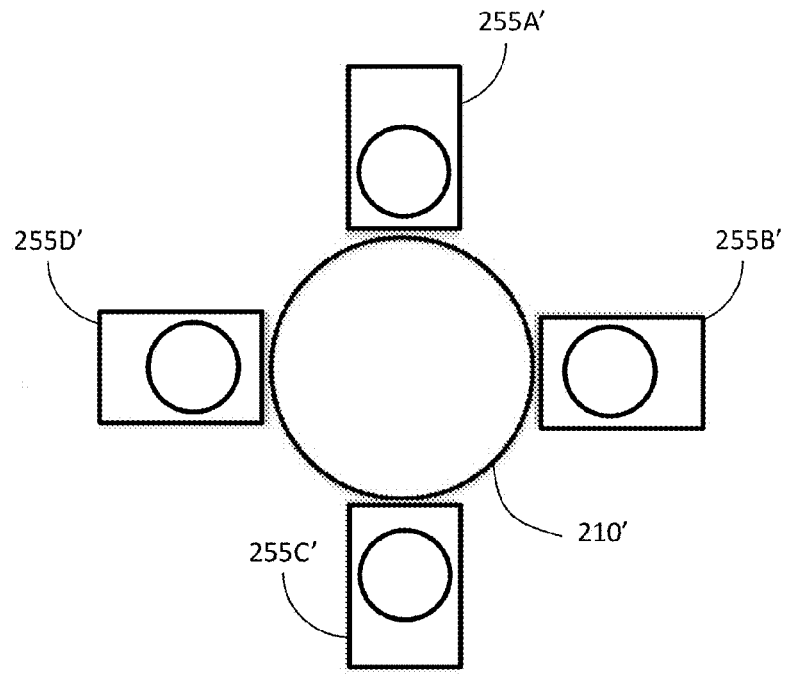
FIG. 4A
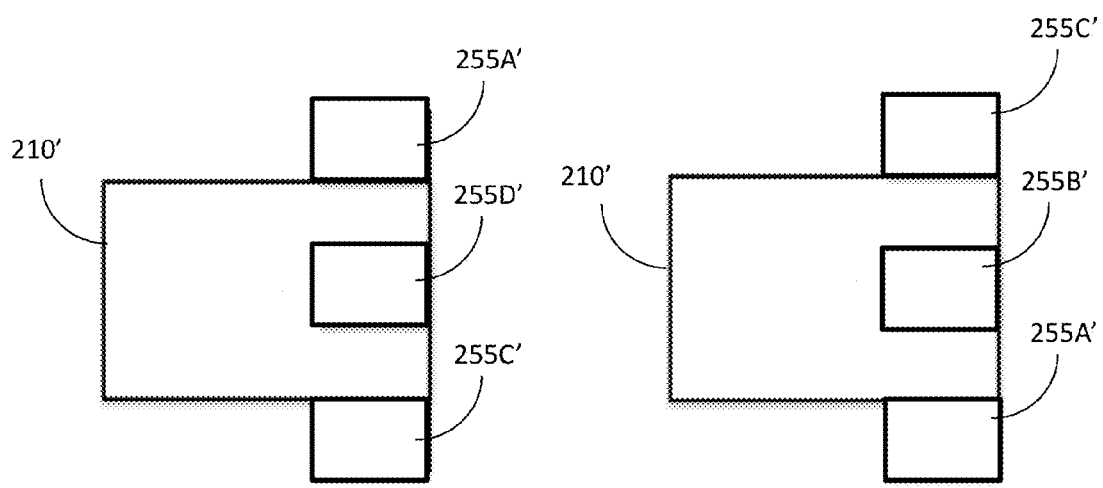
FIG. 4B       FIG. 4C

SYSTEMS AND METHODS FOR DETERMINING BIOMECHANICAL PROPERTIES OF THE EYE FOR APPLYING TREATMENT

CROSS-REFERENCE TO RELATED APPLICATIONS

This application is a continuation-in-part of U.S. application Ser. No. 14/308,678, filed Jun. 18, 2014, which claims priority to: U.S. Provisional Patent Application No. 61/836,211, filed Jun. 18, 2013; U.S. Provisional Patent Application No. 61/836,221, filed Jun. 18, 2013; U.S. Provisional Patent Application No. 61/856,244, filed Jul. 19, 2013; U.S. Provisional Patent Application No. 61/864,087, filed Aug. 9, 2013, the contents of these applications being incorporated entirely herein by reference.

BACKGROUND OF THE INVENTION

1. Field of the Invention

The invention pertains to systems and methods for diagnosing and treating the eye, and more particularly, to systems and methods for measuring biomechanical properties of the eye to plan, implement, and assess treatments of the eye.

2. Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas of weakness in the structure of the cornea. For example, a photosensitizing agent (e.g., riboflavin) is applied to the cornea as a cross-linking agent. Once the cross-linking agent has been applied to the cornea, the cross-linking agent is activated by a light source (e.g., ultraviolet (UV) light) to cause the cross-linking agent to absorb enough energy to cause the release of free oxygen radicals (e.g., singlet oxygen) and/or other radicals within the cornea. Once released, the radicals form covalent bonds between corneal collagen fibrils and thereby cause the corneal collagen fibrils to cross-link and strengthen and stabilize the structure of the cornea. The success of procedures, such as cross-linking treatment, in addressing eye disorders depends on determining accurately the areas of the eye that require treatment and assessing the results of the treatment.

SUMMARY

According to one aspect of the present invention, a system for measuring biomechanical properties of the eye to at least one of plan, implement, or assess treatments of the eye includes a biomechanical measurement system, a corneal tomography system, and an iris imaging system. The eye has an iris and a cornea. The biomechanical measurement system includes a light source configured to provide an incident light and a confocal microscopy system configured to direct the incident light at a plurality of sections of the cornea. The incident light is scattered by the plurality of sections of the corneal tissue. The biomechanical measurement system also includes a spectrometer configured to receive the scattered light and process frequency characteristics of the received scattered light to measure a Brillouin frequency shift in the scattered light. The biomechanical measurement system is configured to determine biomechanical data based on the measured Brillouin frequency shift. The corneal tomography measurement system is configured to measure a corneal tomography of the eye and determine corneal tomography data indicative of the measured corneal tomography. The iris imaging system is configured to image the iris and determine iris image data indicative of the imaged iris. The system also includes one or more processors communicatively coupled to the biomechanical system, the corneal tomography system, and the iris imaging system. The one or more processors includes a processor clock. The system further includes one or more memory devices storing instructions that, when executed by the one or more processors, cause the one or more processors to determine time stamp data, based on the processor clock, for each of the biomechanical data, the corneal tomography data, and the iris image data, store the biomechanical data with the associated time stamp data in the one or more memory devices, store the corneal tomography data with the associated time stamp data in the one or more memory devices, and store the iris image data with the associated time stamp data in the one or more memory devices. The instructions further cause the one or more processors to, for each of the biomechanical data, determine which of the iris image data has the same associated time stamp data and, for each of the corneal tomography data, determine which of the iris image data has the same associated time stamp data. The instructions still further cause the one or more processors to determine three-dimensional voxel data by correlating each of the biomechanical data with each of the corneal tomography data determined to have the same associated iris image data. Each of the three-dimensional voxel data includes an indication of at least one of the biomechanical data, at least one of the corneal tomography data, and at least one of the iris image data.

According to another aspect of the present invention, a system for determining biomechanical properties of corneal tissue includes a light source configured to provide an incident light and a confocal microscopy system configured to scan the incident light across a plurality of cross-sections of the corneal tissue. The incident light is reflected by the plurality of cross-sections of corneal tissue as scattered light. The system also includes a filter or attenuating device configured to block or attenuate the Rayleigh peak frequency of the scattered light, a spectrometer configured to receive the scattered light and process frequency characteristics of the received scattered light to determine a Brillouin frequency shift in response to the Rayleigh peak frequency being blocked or attenuated by the filter or attenuating device, and a processor configured to determine a three-dimensional profile of the corneal tissue according to the determined Brillouin frequency shift. The three-dimensional profile provides an indicator of one or more biomechanical properties of the corneal tissue.

According to still another aspect of the present invention, a method for measuring biomechanical properties of the eye to at least one of plan, implement, or assess treatments of the eye includes directing, via a confocal microscopy system, an incident light from a light source at plurality of sections of the cornea. The incident light is scattered by the plurality of sections of the corneal tissue. The eye has an iris and a cornea. The method also includes receiving the scattered light in a spectrometer, processing frequency characteristics of the received scattered light to measure a Brillouin frequency shift in the scattered light, determining biomechanical data based on the measured Brillouin frequency shift, measuring a corneal tomography of the eye, determining corneal tomography data indicative of the measured corneal tomography, imaging, via an image capture device, the iris, determining iris image data indicative of the imaged iris, determining, based on a processor clock provided by one or more processors, time stamp data for each of the biomechanical data, the corneal tomography data, and the iris image data, storing the biomechanical data with the associated time stamp data in one or more memory devices, storing the corneal tomography data with the associated time stamp data in the one or more memory devices, and storing the iris image data with the associated time stamp data in the one or more memory devices. The method further includes, for each of the biomechanical data, determining which of the iris image data has the same associated time stamp data. The method also includes, for each of the corneal tomography data, determining which of the iris image data has the same associated time stamp data. The method still further includes determining three-dimensional voxel data by correlating each of the biomechanical data with each of the corneal tomography data determined to have the same associated iris image data. Each of the three-dimensional voxel data includes an indication of at least one of the biomechanical data, at least one of the corneal tomography data, and at least one of the iris image data.

According to another aspect of the present invention, a system for measuring biomechanical properties of the eye to at least one of plan, implement, or assess treatments of the eye includes a biomechanical measurement system and a registration system. The biomechanical measurement system includes a light source configured to provide an incident light and a confocal microscopy system configured to direct the incident light at a plurality of sections of a target feature of the eye. The incident light is scattered by the plurality of sections of the target feature of the eye. The biomechanical measurement system further includes a spectrometer configured to receive the scattered light and process frequency characteristics of the received scattered light to measure a Brillouin frequency shift in the scattered light. The biomechanical measurement system is configured to determine biomechanical data based on the measured Brillouin frequency shift. The registration system is configured to determine a three dimensional position of the biomechanical data relative to the system and the eye.

According to yet another aspect of the present invention, a method for measuring biomechanical properties of the eye to at least one of plan, implement, or assess treatments of the eye includes directing an incident light from a light source, via a confocal microscopy system, at a plurality of sections of a target feature of the eye. The incident light is scattered by the plurality of sections of the target feature of the eye. The method also includes receiving the scattered light in a spectrometer, processing frequency characteristics of the received scattered light to measure a Brillouin frequency shift in the scattered light, determining biomechanical data based on the measured Brillouin frequency shift, measuring a tomography of the target feature of the eye, and determining tomographic data indicative of the measured tomography. The method further includes imaging, via an image capture device, one or more anatomical features of the eye or a structured light pattern applied to the eye. The method also includes determining registration data indicative of the imaged one or more anatomical features of the eye or the imaged structured light pattern applied to the eye and determining, based on a processor clock provided by one or more processors, time stamp data for each of the biomechanical data, the tomographic data, and the registration data. The method still further includes storing the biomechanical data with the associated time stamp data in one or more memory devices, storing the tomographic data with the associated time stamp data in the one or more memory devices, and storing the registration data with the associated time stamp data in the one or more memory devices. The method includes, for each of the biomechanical data, determining which of the registration data has the same associated time stamp data and, for each of the tomographic data, determining which of the registration data has the same associated time stamp data. The method also includes determining three-dimensional voxel data by correlating each of the biomechanical data with each of the tomographic data determined to have the same associated registration data. Each of the three-dimensional voxel data includes an indication of at least one of the biomechanical data, at least one of the tomographic data, and at least one of the registration data.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIGS. 4A-4C illustrate stereoscopic cameras and an optical component for the confocal scanning microscopy head illustrated in FIG. 3

Figure 1:
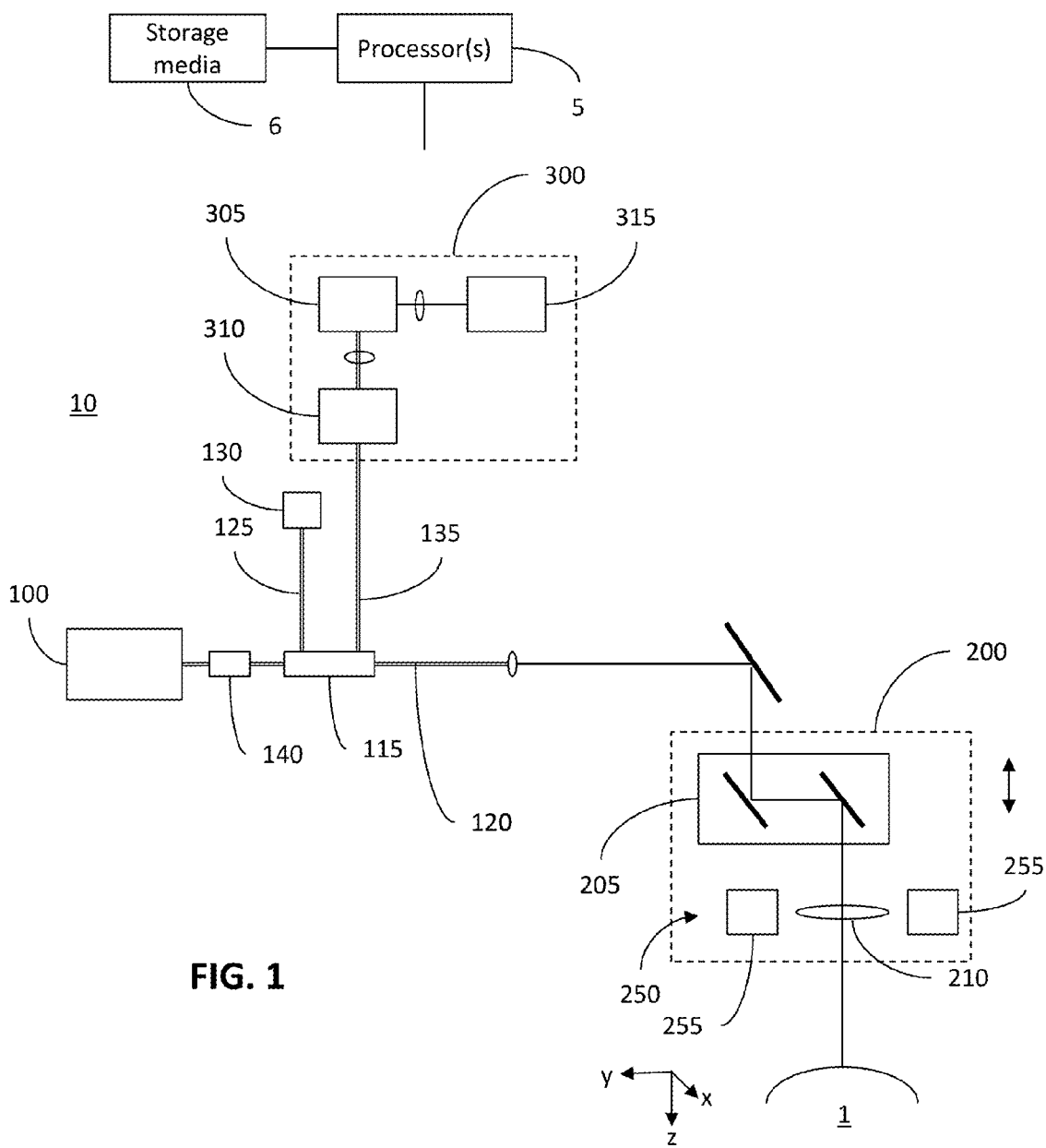
FIG. 1 is a schematic diagram of an example system for measuring biomechanical properties of the eye to plan, implement, and assess treatments of the eye according to some aspects of the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DETAILED DESCRIPTION

Aspects of the present invention relate to systems and methods for measuring biomechanical properties of the eye to plan, implement, and assess treatments of the eye. According to some aspects, the systems and methods provide an approach to developing and implementing a plan for treating an eye disorder. For example, the systems and methods can be employed to accurately determine areas of corneal weakness so that cross-linking treatment can be applied to the most appropriate areas.

According to aspects of the present invention, systems and methods employ the principle of Brillouin scattering to determine biomechanical properties of the eye. Brillouin scattering involves the inelastic scattering of incident light (photons) by thermally generated acoustic vibrations (phonons). Thermal motions of atoms in a material (e.g., solid, liquid) create acoustic vibrations, which lead to density variations and scattering of the incident light. The scattering is inelastic, which means that the kinetic energy of the incident light is not conserved. The photon either loses energy to create a phonon (Stokes) or gains energy by absorbing a phonon (Anti-Stokes). The frequency and path of the scattered light differ from those of the incident light. The frequency shift, known as the Brillouin shift, is equal to the frequency of the scattering acoustic vibration and provides information regarding the properties of the material. In particular, the systems and methods described herein evaluate the Brillouin shift to measure the biomechanical, e.g., viscoelastic, properties of corneal tissue.

Accordingly, FIG. 1 illustrates an example Brillouin spectroscopy system 10 for determining biomechanical properties of an eye via Brillouin scattering. As shown in FIG. 1, the system employs confocal scanning microscopy (CSM). A light source 100 provides incident light for generating Brillouin scattering in an eye 1. The light source 100 may provide a laser with an ultraviolet (UV), visible, or near infrared (NIR) wavelength, depending on the resolution required. In an example embodiment, the light source 100 includes a narrowband linewidth diode laser source (approximately 100 kHz-4 MHz) that generates a laser with a NIR wavelength of approximately 780 nm. This wavelength provides an advantageous compromise of spatial and depth resolution while not being too bright for the patient. The light source 100 is coupled to a single mode beam splitting fiber coupler 115 with a specific input/output power ratio (e.g., approximately 5-20%) and a narrowband frequency (e.g., approximately 100 kHz to approximately 4 MHz). With this beam splitting fiber coupler 115, a percentage of the light from the light source 100 based on the input/output power ratio (e.g., approximately 5-20%) passes to a CSM fiber 120 that is coupled to a CSM head 200, while the rest of the light (e.g., approximately 80-95%) passes to a beam dump fiber 125 which is measured with a photodiode 130. It is understood that different input/power ratios may be employed. In addition, although the example of FIG. 1 employs the beam splitting fiber coupler 115, other embodiments can split the light from the light source 100 using any combination of optical devices, such as a beam splitter, a half wave plate/polarizing beam splitter/quarter wave plate combination, etc.

The CSM head 200 includes a set of scanning galvo mirrors 205 and a confocal imaging lens 210. In some embodiments, to achieve a consistent flat field, the confocal imaging lens 210 may be an F-theta lens which may have a focal length on the order of approximately 1 cm to approximately 20 cm. In general, however, the system 10 employs a confocal imaging lens 210 with an appropriate focal length to provide a suitable working distance to the eye 1. The light passing through the fiber 120 is collimated and directed through the set of scanning galvo mirrors 205 where it is then collimated to a spot on the eye 1 via the confocal imaging lens 210. The set of scanning galvo mirrors 205 is used in combination with the confocal imaging lens 210 to scan multiple points of the cornea in enface X-Y slices. For example, a first enface X-Y scan of a specified number of points in a specified pattern is made in a plane starting at the apex of the cornea. The CSM head 200 is then stepped a known distance in the Z-direction (toward the eye 1) to create a second additional enface X-Y scan of the cornea. Subsequently, the CSM head 200 is iteratively stepped in the Z-direction to create additional (e.g., third, fourth, etc.) enface X-Y scans of the cornea for the full thickness of the cornea out to a user specified diameter. Specific regions of interest may be specified for the scanning based on corneal tomography images or other corneal analysis.

It should be understood that the scanning pattern is not restricted to strictly enface imaging. For example, the system can first scan in the z dimension and then step in X-Y dimensions or some other raster scan pattern. Additionally, for example, the first enface X-Y scan can be made in a plane starting at a user defined diameter and then stepped toward the apex of the cornea.

The incident light from the light source 100 experiences scattering when it interacts with the eye 1, i.e., corneal tissue. The light scattered back from the spot of incident light on the eye 1 is directed back through the confocal imaging lens 210 and the set of galvo mirrors 205 and into the beam splitting fiber coupler 115 where the fiber core acts like a pinhole in a confocal scanning microscope. The scattered light is then transmitted back through the beam splitting fiber coupler 215 where approximately 80-95% of the scattered light is directed in a spectrometer single mode fiber 135, while the rest of the scattered light (approximately 5-20%) heads to the laser. The laser is equipped with an optical isolator 140 so that the scattered light from the eye 1 does not create feedback within the laser resonator causing potential laser instability.

The spectrometer input fiber 135 extends to a spectrometer system 300 and may have any length to separate spectrometer system 300 practically from other aspects of the system 10, e.g., the light source 100, the CSM head 200, etc. The spectrometer system 300 includes a tilted virtual imaged phased array (VIPA) 305 of a known thickness and free spectral range. The VIPA 305 receives the scattered light from spectrometer input fiber 135 via a lens or lens system.

As described above, the incident light from the light source 100 experiences scattering when it interacts with the corneal tissue. This scattering includes Brillouin scattering and the resulting Brillouin shift can be analyzed to determine biomechanical, e.g., viscoelastic, properties of the corneal tissue. The scattering, however, also includes the additional phenomenon of Rayleigh scattering, which involves elastic scattering of the incident light. This elastically scattered light has the same frequency as the incident light. In addition, the elastically scattered light is orders of magnitude more intense than the Brillouin-scattered light, and the frequency shift between the scatter fractions is very low, e.g., only a few GHz. As such, Brillouin spectroscopy requires separating the Brillouin-scattered light frequencies from the Rayleigh-scattered light frequency.

The system 10 employs the VIPA 305 to separate the Brillouin-scattered light frequencies (Stokes and Anti-Stokes) from the Rayleigh-scattered light frequency. After separation, the light exits the VIPA 305 where it is collected and collimated with a lens or lens system and imaged onto a line scan camera 315 (properly filling the pixels of the line scan camera 315). The pixels of the line scan 315 are calibrated for a specific frequency shift per pixel (e.g., 0.15 GHz/px). In this way, the line scan camera 315 acts like a ruler that measures the changing shifts of the Brillouin frequencies with respect to the Rayleigh frequency of the cornea. The line scan camera 315 can be calibrated by measuring standards with known Brillouin frequency shifts. The line scan camera 315 has a given pixel array dimension typically with 512, 1024, or 2048 pixels that is very sensitive to the wavelength of the illumination to allow for short integration times. Therefore, the line scan camera 315 may provide specific methods for increasing sensitivity such as cooling, increased pixel size, etc.

The shift in frequency measured by the line scan camera 315 between the Brillouin frequencies (Stokes and Anti-Stokes) and the Rayleigh frequency is a measure of the bulk modulus or stiffness properties of the cornea. Thus, with the Brillouin spectroscopy system 10, a mapping of the biomechanical properties of the cornea can be made. Mappings can be conducted and compared for normal, diseased, and treated (e.g., cross-linking treated) corneas as well as a quantitative measure of anterior segment anatomy.

A specific approach for increasing sensitivity and shortening exposure times to allow for increased data acquisition rates involves either blocking or attenuating the Rayleigh peak. This allows the highest gain on the line scan camera 315 to be utilized without saturation. Example approaches for blocking or attenuating the Rayleigh peak are summarized in FIG. 7. In step 505, scattered light is received from a confocal imaging system directed at an eye, and after the Raleigh peak is blocked or attenuated (steps 510A, 510B, or 510C), the scattered light is eventually imaged onto line scan camera 315 in step 515.

Figure 7:
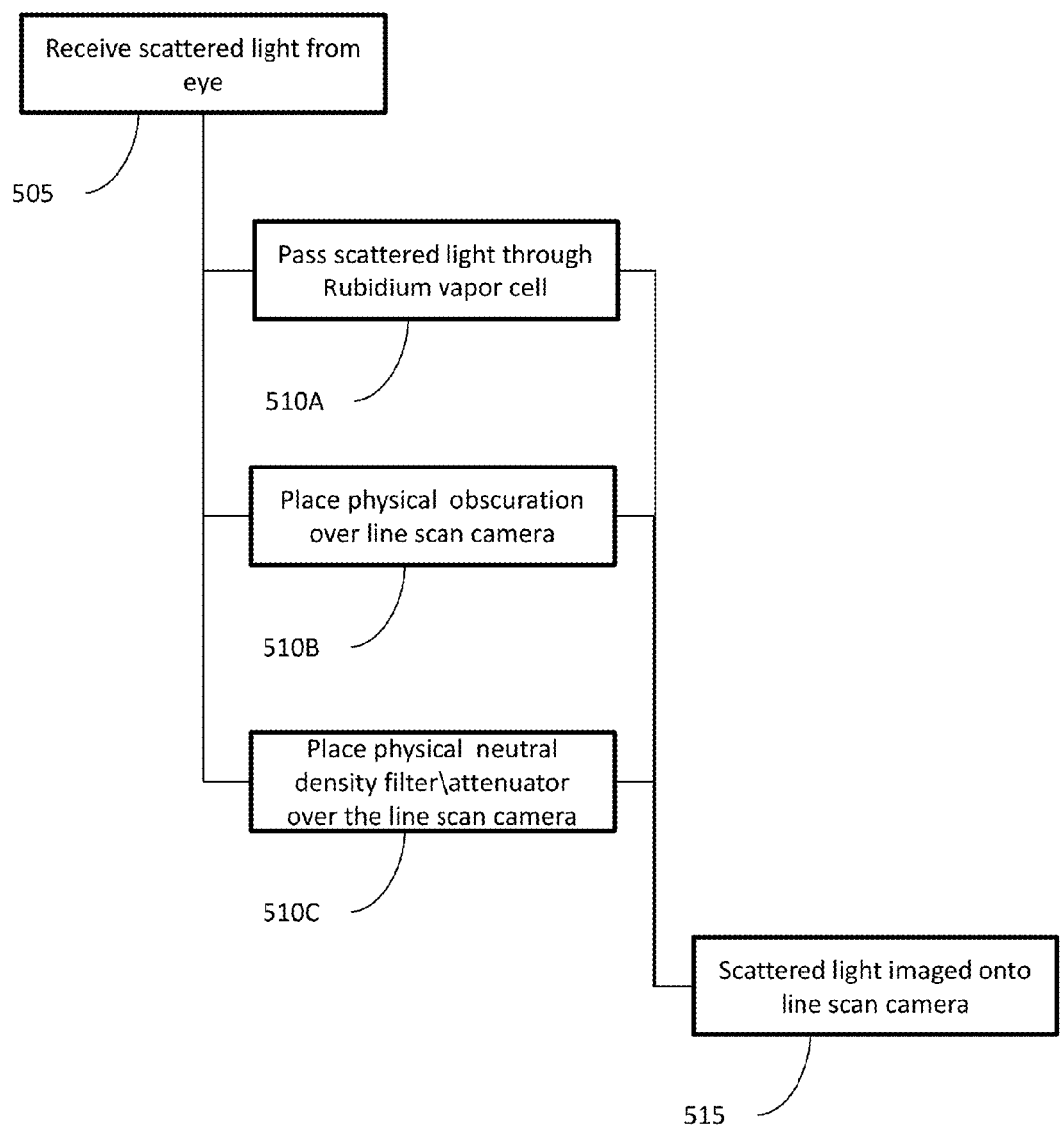
FIG. 7 is a schematic diagram of example approaches for blocking or attenuating the Rayleigh peak in scattered light according to some aspects of the present invention.

One example approach 505A shown in FIG. 7 for blocking the Rayleigh peak involves employing a Rubidium vapor cell in-line with the optical system. As shown in FIG. 1, for example, the scattered light from the spectrometer input fiber 135 passes through a Rubidium vapor cell 310, which is tuned to block the Rayleigh frequency. In particular, the Rubidium vapor cell 310 is tuned to the Rayleigh frequency with a known amount of absorption to match the amplitude of the Brillouin frequencies. As such, the Rubidium vapor cell tuned to the Rayleigh frequency acts as a narrowband notch filter, eliminating this peak from the spectrum hitting the line scan camera 315. Advantageously, the Rubidium vapor cell removes noise and improves signal-to-noise ratio. The Brillouin frequency shift is then measured by taking the frequency difference between the Stokes and Anti-stokes Brillouin peaks and dividing by two.

Another example approach 505B shown in FIG. 7 for blocking the Rayleigh peak puts a narrow physical obscuration over the line scan camera pixels associated with the Rayleigh peak. Again, the Brillouin frequency shift described above is measured by taking the frequency difference between the Stokes and Anti-stokes Brillouin peaks and dividing by two.

A similar approach 505C shown in FIG. 7 for attenuating the Rayleigh peak involves putting a narrow physical neutral density filter or attenuator over the line scan camera pixels associated with only the Rayleigh peak. In this way, the Rayleigh peak is attenuated to the same order of magnitude as the Brillouin peaks. As such, the frequency shift between the Stokes, Anti-Stokes, and Rayleigh peaks can be better determined through redundant measure allowing for higher noise floor signal and higher sensitivity. In addition, the relative amplitude of the peaks between the Stokes, Anti-Stokes, and Rayleigh peaks may be used to help increase and normalize the contrast associated with morphological imaging of the corneal structures.

The ratio of the Rayleigh peak to the Brillouin peak is called the Landau-Placzek Ratio and is a measure of the turbidity of the tissue. Therefore, by tuning the Rubidium absorption filter to absorb a predicted amount of the Rayleigh frequency or using a partially reflective/transmitting obscuration, a quantitative measure of the turbidity of the cornea can be made. This is essentially a densitometry measure of the cornea. The densitometry of the cornea in conjunction with the biomechanical properties of the cornea gleaned from the Brillouin frequency shift may give an enhanced measure of corneal disease states as well as a better measure of the amount of corneal cross-linking imparted to the cornea.

Accordingly, aspects of the present invention employ a confocal scanning microscopy system and a spectrometer system to measure the frequency differences between Brillouin-scattered light and the Rayleigh-scattered light. In the case of the cornea, the Brillouin shift is on the order of approximately 2 GHz to approximately 10 GHz. As described above, Brillouin spectroscopy systems and methods can be employed to determine accurately areas of corneal weakness so that cross-linking treatment can be applied to the most appropriate areas. Such systems and methods may also be used during and/or after the cross-linking treatment for real-time monitoring of the cross-linking activity as well as healing processes over time. Through the scanning process, a real-time image of the cornea can be constructed allowing for anatomical measurements of various tissues such as tear film, epithelium, stroma, etc.

During the scanning process, the patient's head may be stabilized through the use of a head and chin rest system (not shown) typically used for many ophthalmic diagnostic and therapeutic devices. The head and chin rest system holds the patient's head and eye socket relatively still. The patient's eye, however, can still move within the eye socket. To address such movement of the eye 1, the system 10 may employ a stereo range finding (SRF) module 250 that includes a pair (or pairs) of cameras 255 separated by a known distance viewing the same field of view. As the spot of incident light moves across the cornea, the scanning pattern is seen by the cameras. The disparity between the images from the cameras 255 and the expected position based on scanning parameters is a measure of the X-Y-Z position of the particular X-Y scan (defined as the X-Y-Z composite scan). The X-Y-Z composite scan can then be placed in a series of predetermined three dimensional bins (or voxels) for the cornea. The system captures data until enough X-Y-Z composite scans have filled all the bins. These bins are then averaged and the composite corneal mapping of the Brillouin frequency shifts is used to calculate the viscoelastic mapping and other quantitative measures of the cornea. As such, the system 10 continues to scan until all the data is collected, automatically stopping only when all the bins have been filled. In general, the bins represent different three-dimensional sections of the cornea and measurements for each section are associated with the respective bin. Any number of measurements (0, 1, 2, 3, etc.) can be recorded for each bin as desired and the bins can have the same or different numbers of measurements. In addition, the sizes of the bins can vary from very course (e.g., 1 mm×1 mm×100 μm) to very fine (e.g., 25 μm×25 μm×25 μm) depending on requirements for analysis. For example, routine examination of a healthy eye may permit the use of more coarsely sized bins, which typically means that there are fewer bins and less time is required to obtain measurements. The bins can be defined across any area of the cornea, e.g., approximately 9.5 mm to 14 mm across the corna extending to the sclera.

Accounting for the various amounts of motion of the eye 1 allows the patient to be positioned and the eye 1 to be scanned in a single measurement period. This approach reduces, if not eliminates, the number of repeat measurements requiring repositioning of the patient, in contrast to other diagnostic systems such as corneal tomography systems which often require the patient to be repositioned several times to obtain a quality image.

It should be understood that, according to additional and/or alternative aspects of the present invention, the corneal tomography can be measured by other systems. For example, an alternative to utilizing the scanned beam is to project a static grid at a different wavelength to determine the three dimensional volume of the cornea using the same stereo pair cameras.

Mapping of the Brillouin shifts gives a biomechanical mapping of the viscoelastic properties of the tissue. The mapping of the Brillouin shifts may be registered using the pair of cameras 255 which allows for three dimensional registration of the points as they are taken, especially in the case where the data acquisition is slow. In this manner, eye movement taken into account.

Figure 2:
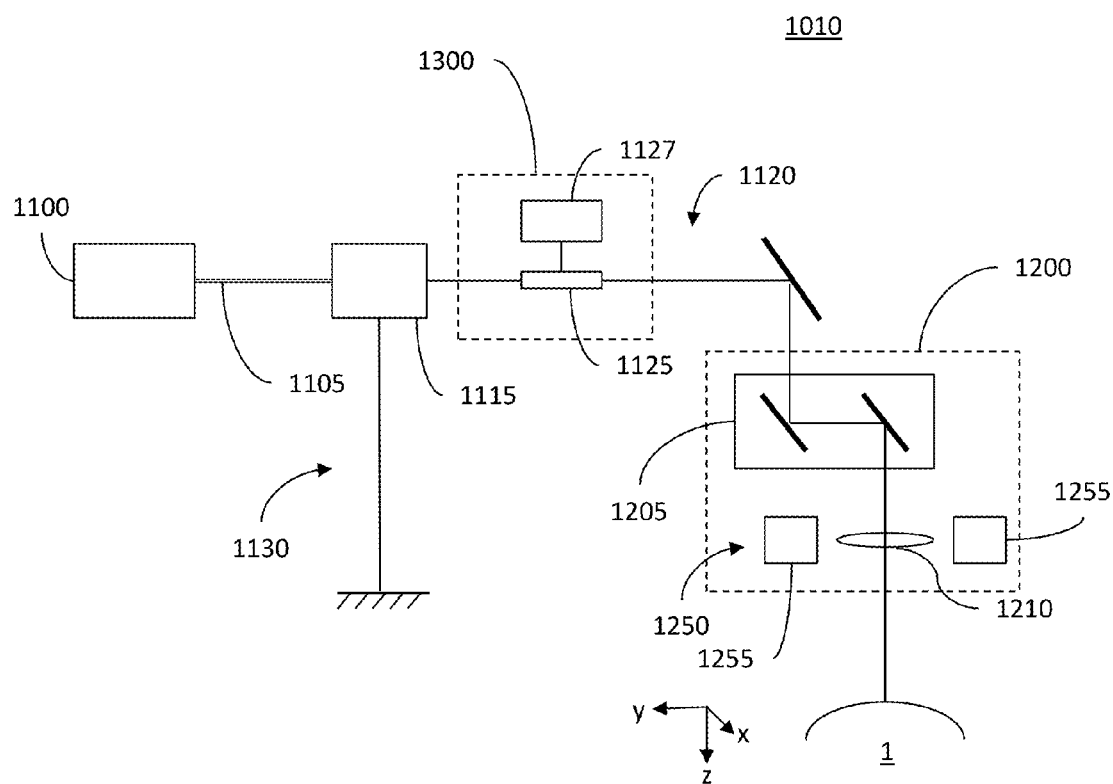
FIG. 2 is a schematic diagram of an example system for measuring biomechanical properties of the eye to plan, implement, and assess treatments of the eye according to additional aspects of the present invention.

Referring to FIG. 2, an alternative embodiment for a Brillouin spectroscopy system 1010 is illustrated. In contrast to the system 10 shown in FIG. 1, the system 1010 employs a technique similar to an optical coherence tomography (OCT) system 1305. OCT is an optical signal acquisition and processing method. It captures micrometer-resolution, three-dimensional images from within optical scattering media (e.g., biological tissue). Optical coherence tomography is an interferometric technique, typically employing near-infrared light. The use of relatively long wavelength light allows it to penetrate into the scattering medium. Depending on the properties of the light source, optical coherence tomography can achieve sub-micrometer resolution.

As shown in FIG. 2, the system 1010 includes a swept source laser system 1100, which, for example, may provide a bandwidth of approximately 80 nm to approximately 150 nm or more. The wavelength of the laser from the laser system 1100 may be ultraviolet (UV), visible, or near-infrared (NIR) depending on the resolution required. The laser system 1100 is coupled to a single mode optical fiber 1105 with narrowband frequencies for the individual lines of the swept source. In one embodiment, a laser provides a NIR bandwidth, which advantageously offers sufficient spatial and depth resolution while not being too bright for the patient.

In an OCT system, the laser from the optical fiber 1105 would be split by a beamsplitter into two arms, a sample arm (directed to the sample of interest) and a reference arm (usually a mirror), where the light reflected back from the sample through the sample arm and reference light in the reference are produce an interference pattern. In the embodiment of FIG. 2, the laser from the optical fiber 1105 may be split by a beamsplitter 1115 into a sample arm 1120 and a reference arm 1130. The sample arm 1120 is employed for Brillouin spectroscopy. In particular, the sample arm 1120 includes a CSM head 1200. The CSM head 1200 includes a set of scanning galvo mirrors 1205 and a confocal imaging lens 1210. In some embodiments, to achieve a consistent flat field, the confocal imaging lens 1210 may be an F-theta lens which may have a focal length on the order of approximately 1 cm to approximately 20 cm. In general, however, the system 1010 employs a confocal imaging lens 1210 with an appropriate focal length to provide a suitable working distance to the eye 1. The F-theta lens may also have a large chromatic aberration. The light in the sample arm 1120 is directed through the set of scanning galvo mirrors 1205 where it is then collimated to a spot on the eye 1 via the confocal imaging lens 1210. The set of galvo mirrors 1205 is used in combination with the confocal imaging lens 210 to scan multiple points of the cornea in enface X-Y slices. Enface X-Y scans of a specified number of points in a specified pattern are made in planes starting at the apex of the cornea. As the swept source laser is then scanned, this naturally generates scans along the Z-direction through the tissue. The length of the Z scan is determined by the design parameters of the individual components and is optimized to meet the design criteria of the tissue being measured.

The incident light from the light source 1100 experiences scattering when it interacts with the eye 1, i.e., corneal tissue. The light scattered back from the spot of incident light on the eye 1 is directed back through the confocal imaging lens 1210 and the set of galvo mirrors 1205.

The system 1010 includes a spectrometer system 1300. Rather than employing a VIPA to identify and separate frequencies in the scattered light, however, the spectrometer system 1300 employs a modulated fiber Bragg grating (FBG) 1125 in the sample arm 1120, which may have any number of grating structures to match the conditions of the desired imaging of the tissue. A radio frequency source 1127 is employed to modulate the FBG through stress induction where the grating period is modulated at very high frequencies. High speed electronics are utilized to analyze the output signals.

Raman scattering is another phenomenon involving inelastic scattering processes of light with vibrational properties of matter. The detected frequency shift range and type of information extracted from the sample, however, are different. Brillouin scattering denominates the scattering of photons from low-frequency phonons, while for Raman scattering, photons are scattered by interaction with vibrational and rotational transitions in single molecules. Therefore, Brillouin scattering and Raman scattering provide different information about the sample. Raman spectroscopy is used to determine the chemical composition and molecular structure, while Brillouin scattering measures properties on a larger scale, such as the elastic behavior. The fiber structure and modulation of the FBG 1125 is matched and made in such a way as to create a super heterodyned beat frequency between the Stokes and Anti-Stokes peaks in the Brillouin scattering. In particular, the radio frequency source 1127 can be modulated to sweep through a range of frequencies to identify a beat frequency associated with the Stokes and Anti-Stokes peaks. In particular, the radio frequency source 1127 can be similarly modulated to sweep through a range of frequencies to identify a beat frequency associated with the Raman peaks. This beat frequencies associated with the Stokes and Anti-Stokes peaks and the Raman peaks can then be used to determine the Brillouin and Raman shifts. Mapping of the Brillouin and Raman shifts give a morphological and biomechanical mapping of the properties of the tissue.

Figure 3:
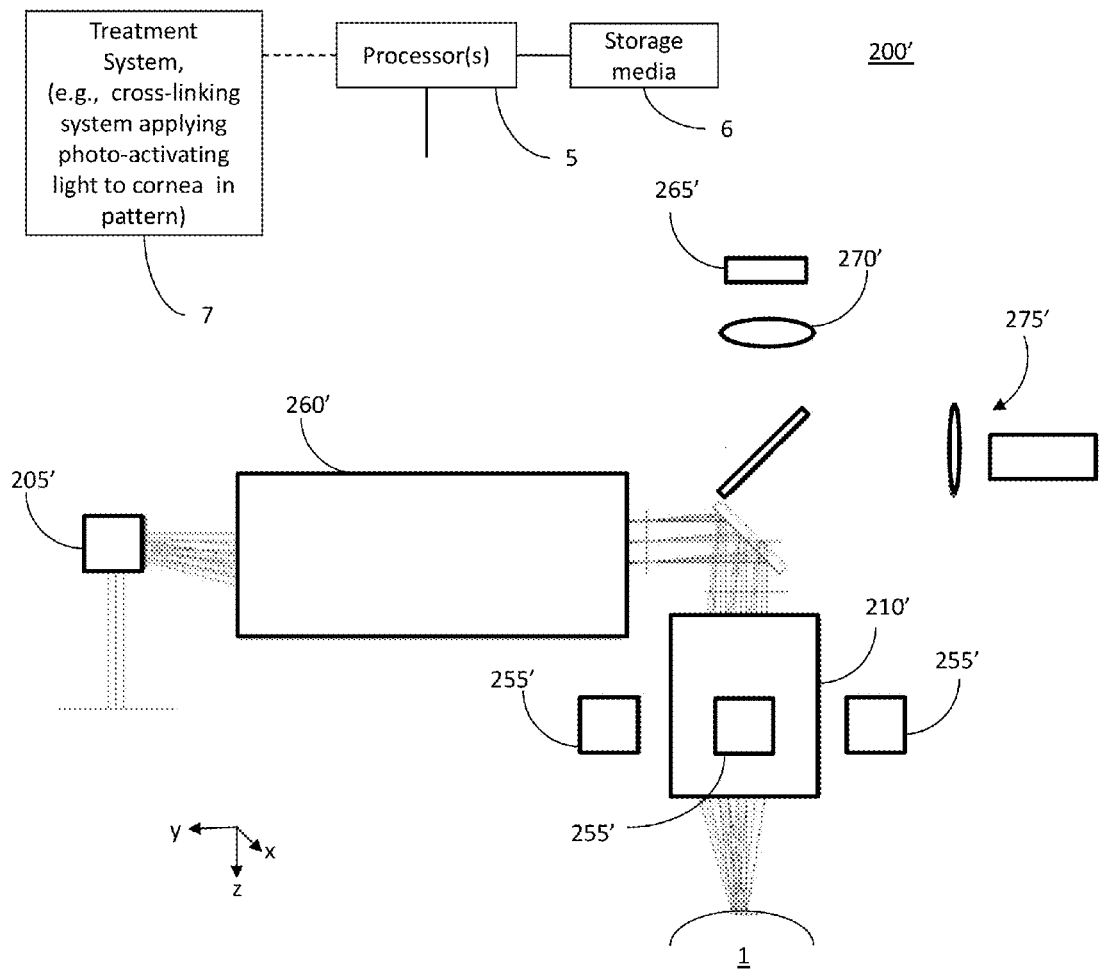
FIG. 3 is a schematic diagram of an example confocal scanning microscopy head for measuring biomechanical properties of the eye to plan, implement, and assess treatments of the eye according to some aspects of the present invention.

Referring now to FIG. 3, a schematic diagram of an alternative example CSM head 200' is illustrated according to some aspects of the present invention. The CSM head 200' advantageously integrates aspects of the Brillouin measurement components described above as well as corneal tomography measurement components and iris imaging components for the system 10, 1010. With respect to Brillouin aspects of the system 10, 1010, the CSM head 200' can include a set of scanning galvo mirrors 205', a beam expander 260', and a confocal imaging lens 210' (e.g., a F-theta lens). The light from the light source 100, 1100 is received in the CSM head 200' and directed to the set of scanning galvo mirrors 205'. The light can be collimated prior to being received in the CSM head 200' or, alternatively, the CSM head 200' can include optical components for collimating the light that is directed to the set of scanning galvo mirrors 205'. The set of scanning galvo mirrors 205' are communicatively coupled to a processor(s) 5 that is configured to control the X-Y positioning of the light relative to the target corneal tissue. The collimated light from the set of scanning galvo mirrors 205' is then directed to the beam expander 260', which enlarges the collimated light. The enlarged collimated light is directed from the beam expander 260' to the confocal imaging lens 210', which focuses the light to a focal plane within the corneal tissue (i.e., a Z-dimension distance). As further illustrated in FIG. 3, the light scattered by the corneal tissue is collected by the confocal imaging lens 210', passed back through the optical components of the CSM head 200', and directed to the spectrometer system 300, 1300 for analysis. The measured biomechanical property information can be determined by the processor(s) 5 (as described above) and stored in a memory as biomechanical data (e.g., viscoelastic data).

With respect to corneal tomographic aspects of the system, the CSM head 200' includes a plurality of stereoscopic cameras 255A'-255D' configured to capture images of the corneal tissue. As shown in FIGS. 4A-4C, four stereoscopic cameras 255A'-255D' are located around the confocal imaging lens 210' at 90 degree angles relative to each other. It should be understood that more or fewer stereoscopic cameras 255A'-255D' can be utilized according to some alternative aspects of the present invention. The stereoscopic cameras 255A'-255D' capture respective images of the corneal tissue and the iris of the eye 1, which can be processed (e.g., by analyzing disparities between two or more images via the processor(s) 5) to determine information (e.g., an elevation map) for the anterior surface of the cornea and the posterior surface of the cornea. This corneal surface information can be further processed to determine the corneal pachymetry and, thus, the corneal tomography of the eye 1. The measured corneal tomography can be determined by the processor(s) 5 and stored in the memory as corneal tomography data.

It should be understood that, according to additional and/or alternative aspects of the present invention, the corneal tomography can be measured differently. For example, an alternative to utilizing a scanned beam is to project a static grid at a different wavelength to determine the three dimensional volume of the cornea using the same stereo pair cameras.

With respect to the iris imaging aspects of the system, the CSM head 200' includes an image capture device 265' (e.g., a charge-coupled device (CCD)) and imaging optics 270' for capturing an image of the iris. The processor(s) 5 can determine and store the iris image information as iris image data in the memory. The iris image data provides an indication of the orientation of the eye 1 (i.e., the cornea and the iris) as will be described in greater detail below. Additionally, for example, the iris image data can be utilized for additional X-Y dimension and rotational tracking of the eye 1.

The CSM head 200' can further include a light fixation system 275' that is configured to assist in aligning the target eye with respect to the optical components of the CSM head 200' (e.g., the image capture device 265', the stereoscopic cameras 255A'-255D', and the confocal imaging lens 210'). The light fixation system 275' is configured to project a target light onto an optical component (e.g., a beamsplitter) within the field of view of the target eye. Focusing on the visual target provided by the target light aligns the patient's eye with the optical components of the CSM head 200'. The first, second, third and fourth order Purkinje images of the fixation may be utilized for additional X-Y dimension and rotational tracking of the eye.

The CSM head 200' in concert with the other optical components (e.g., the spectrometer 300, 1300) of the system 10, 1010 provides an integrated system configured to determine both biomechanical data and corneal tomography data for an eye. While these distinct types of data can be analyzed independently of each other to inform the conditions of a patient's eye, the systems and methods of the present invention can advantageously correlate the distinct data sets to develop a significantly improved treatment plan or assessment of eye conditions. For example, the systems and methods of the present invention can correlate the biomechanical data to the corneal tomography data to indicate the viscoelastic properties (e.g., corneal strength) associated with particular anatomical features indicated by the tomography data.

A problem is presented, however, in that the biomechanical data and the corneal tomography data may not be directly correlated. For example, the biomechanical data derived from the measured Brillouin scattering frequencies and the corneal tomography data derived from the captured stereographic images may be captured at different points in time or over different durations. Because the patient's eye may move during the measurement procedures, the position and/or orientation of a map of the biomechanical data may differ from that of the corneal tomography data. Additionally, for example, while the biomechanical data is derived from a confocal system that scans point by point over successive X-Y planes stepped in a Z direction, the corneal tomography data can be derived from one or more stereographic images captured over one or more areas of the cornea.

In the systems and methods described herein, a clock is maintained (e.g., via the processor(s) 5) so that all measurements for the biomechanical data and the corneal tomography data are made at known times. Additionally, the iris image capture system 265', 270' obtains the iris image data at all known times for which the biomechanical data and the corneal tomography data is measured. Because the iris has distinct anatomical features, the iris image data provides an indication of the orientation of the eye 1 (and, thus, the corneal tissue) at each point in time. Accordingly, the iris image data at each known point in time is utilized to provide a common frame of reference against which the biomechanical data and corneal tomography data can be translated. In other words, the biomechanical data and the corneal tomography data can be aligned against the iris image data to determine a set of 3D voxel data representing at least the biomechanical data, corneal tomography data, and iris image data for the eye 1. The 3D voxel data thus correlates the measured biomechanical data, corneal tomography data, and iris image data.

The 3D voxel data can be processed (e.g., via the processor(s) 5) to determine a treatment plan for correcting a condition of the eye 1. As one non-limiting example, a finite element analysis can be employed to create the treatment plan. Such a treatment plan can provide a new detailed analysis of how the viscoelastic properties (or other biomechanical properties) of the eye 1 may correspond to the anatomical features indicated by the corneal tomography. As such, a more informed and effective treatment plan or eye condition assessment can be developed by the systems and methods of the present invention.

According to further aspects of the present invention, the treatment plan can be programmed into an eye treatment system to correct a condition of the eye 1. For example, the eye treatment system can include a cross-linking system, a LASIK system, a thermokeratoplasty system, combinations thereof, and/or the like. One non-limiting example of a suitable cross-linking system is the PIXL system manufactured by AVEDRO, Inc. (Waltham, Mass.). The eye treatment system includes an eye tracking system that is configured to monitor the patient's iris.

Advantageously, because the treatment plan data is based on the 3D voxel data and thus the iris image data, the eye treatment system can be automatically aligned to the treatment plan data based on the real-time monitoring of the patient's iris by the eye treatment system. That is, the real-time imagery obtained by the eye treatment system can be aligned with the iris image data of the treatment plan to automatically match patterned eye treatment therapies applied by the eye treatment system to the patient's cornea. For example, the patterns of photoactivating light applied by the PIXL system to the cornea to initiate cross-linking of the corneal fibers can be automatically determined, oriented, and aligned with the patient's cornea based on the real-time monitoring of the patient's eye and the treatment plan data. As shown in FIG. 3, the processor(s) 5 may provide 3D voxel data to a treatment system 7, for example, a cross-linking treatment system that determines a desired pattern of cross-linking activity for the cornea and applies photo-activating light accurately according to the pattern. Approaches for patterned application of photo-activating light can be found, for example, in U.S. patent application Ser. No. 13/438,705, filed Apr. 3, 2012, the contents of which are incorporated entirely herein by reference.

Notably, this automatic alignment of the eye treatment system 7 to the eye treatment plan can mitigate problems associated with cyclotorsion. For example, if a patient is sitting upright during an initial measurement by the system 10, 1010 but laying down during the eye treatment, cyclotorsion can cause the cornea to be in different rotational orientations with respect the system 10, 1010 as compared to the eye treatment system 7. This variance in rotational orientation is accounted for to accurately apply the eye treatment based on the eye treatment plan. As described above, the systems and methods of the present invention can automatically account for such rotational misalignment.

In the example described above, the image capture device 265' is configured to capture an image of the iris from which iris image data is determined. The iris data can be processed, as described above, to develop a treatment plan and automatically align an eye treatment system implementing the treatment plan. According to additional and/or alternative aspects of the present invention, the image capture device 265' can be configured to image other anatomical features of the eye suitable for determining an orientation of the eye 1 (e.g., one or more scleral arteries, scleral veins, retinal arteries, retinal veins, limbus boundary, scleral boundary, etc.). Accordingly, the iris imaging aspects described above can be more generally characterized as registration aspects of the systems and methods of the present invention. Thus, according to additional and/or alternative aspects, the image capture device 265' can image any anatomical feature(s) of the eye having a distinguishing texture such that the image of the iris described above can be more generally characterized as a registration image and the iris image data described above can be more generally characterized as registration data.

Figure 8:
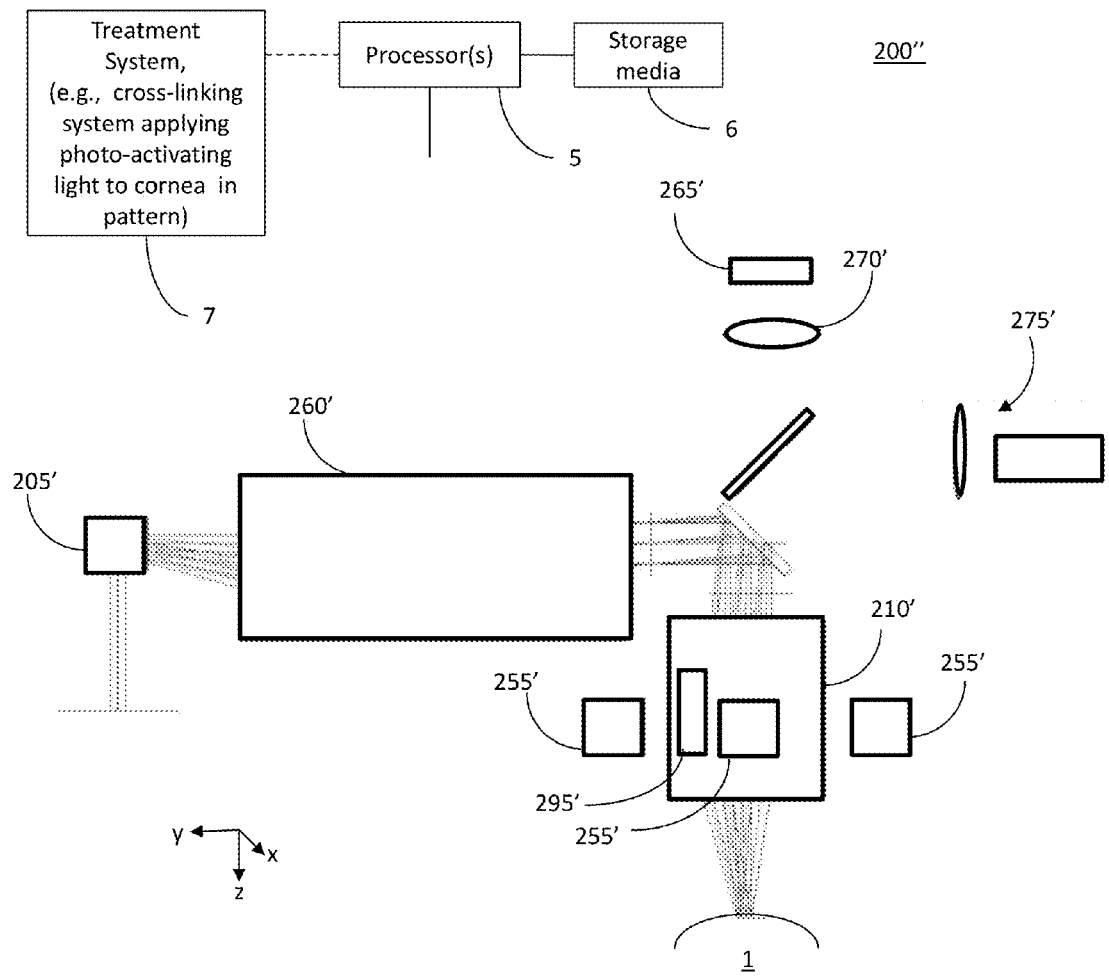
FIG. 8 is a schematic diagram of an example confocal scanning microscopy head for measuring biomechanical properties of the eye to plan, implement, and assess treatments of the eye according to some aspects of the present invention.

As described above, the registration aspects of the systems and methods of the present invention can be based on imaging of anatomical features. According to additional and/or alternative aspects, the registration aspects of the systems and methods of the present invention can be additionally and/or alternatively based on imaging of external information applied to the eye 1. In particular, for example, a structured-light device 295' can be employed to apply a structured light pattern onto a surface of the eye 1. FIG. 8 illustrates a CSM head 200" that is substantially the same as the CSM head 200' but with the addition of a structured-light device 295'. The structured-light device 295' is illustrated as being positioned adjacent to the confocal imaging lens 210'; however, it should be understood that the structured-light device 295' can be positioned in any other location allowing the structured light pattern to be applied to the surface of the eye 1. As non-limiting examples, the structured light pattern can include one or more lines, strips, segmented lines, grids, dots, combinations thereof, etc. Additionally, the structured light pattern can be coded to further distinguish aspects of the structured light pattern. For example, the coding can include embedding sub-patterns or segmentation into horizontal and/or vertical lines of a structured light pattern.

The structure light pattern is distorted by the surface of the eye 1 to form a distorted light pattern. The image capture device 265' captures a registration image including the distorted light pattern on the eye 1. The registration image can be processed via the processor 5 to measure an amount of distortion of the structured light pattern (e.g., based on differences between the distorted light pattern and the structured light pattern), which can provide an indication as to the position and orientation of the eye 1 at the known times at which the biometric and tomographic measurements are made. Accordingly, in the CSM head 200" of FIG. 8, the registration data employed for treatment plans and eye treatment therapies (as described above) is determined by applying the structured light pattern to the surface of the eye 1, imaging the resulting distorted light pattern, and processing the captured registration image of the distorted light pattern.

It should be understood that, according to some aspects, the eye treatment system 7 can also include a structured-light device '295 to apply the structured light to the eye 1 to automatically align the eye treatment system 7 as described above. It is also contemplated that if a structured-light device 295' is employed, the structured light pattern applied to the surface of the eye 1 can be additionally and/or alternatively utilized by the corneal tomographic aspects of the CSM head 200'. For example, the stereoscopic cameras 255A'-255D' can image and process the distorted light pattern to determine the corneal tomography data. In one non-limiting implementation, the corneal tomography data can be based on differences determined between the structured light pattern applied by the structured-light device 295' and the imaged distorted light pattern. In another non-limiting implementation, the imaged distorted light pattern can be utilized to facilitate the stereoscopic analysis of the two or more images captured by the stereographic cameras 255A'-255D' (i.e., point matching between images).

In view of the foregoing, it should be understood that a registration system including the image capture device 265' and the imaging optics 270' is employed to determine the registration data based on imaging of one or more anatomical features and/or one or more external information features. The registration system can be employed to achieve the registration functionalities described with respect to the iris imaging herein, including to determine a three dimensional position of the biomechanical data relative to the system and the eye.

Figure 5:
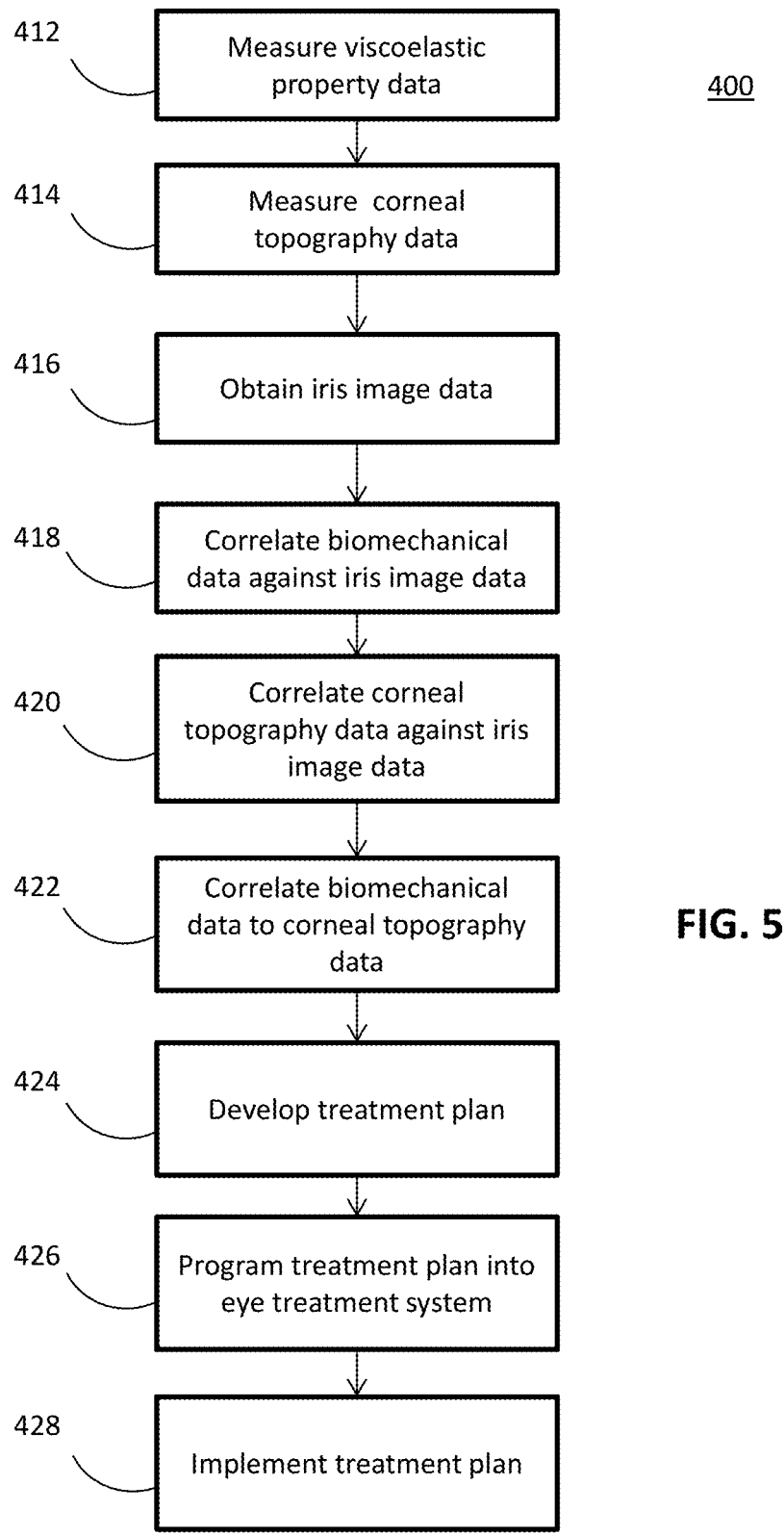
FIG. 5 is a flow chart of an example method for measuring biomechanical properties of the eye to plan, implement, and assess treatments of the eye according to some aspects of the present invention.

Referring now to FIG. 5, a flow chart for an example method 400 for measuring biomechanical properties of the eye to plan, implement, and assess treatments of the eye 1 is illustrated according to some aspects of the present disclosure. At step 412, the biomechanical data is measured for a cornea. As described above, the biomechanical data can be measured by a CSM head (e.g., the CSM head 200 or the CSM head 200') and a spectrometer (e.g., the spectrometer 300 or the spectrometer 1300). The clock provided by the processor(s) 5 determines time data (i.e., time stamp data) such that each biomechanical data point measured is associated with a known measurement time. The biomechanical data and the associated time data can be stored in a memory.

At step 414, the corneal tomography data is measured for the cornea. As described above, the corneal tomography data is measured by the plurality of stereoscopic cameras 255' at known measurement time(s). The corneal tomography data and the associated time data can be stored in the memory.

At step 416, the iris image data is obtained for all known times at which the biomechanical data is measured and all known times at which the corneal tomography data is measured. As described above, the iris image data can be obtained by the image capture device 265' having a field of view configured to be aligned with the eye 1. The iris image data and the associated time data can be stored in the memory.

At step 418, each point of biomechanical data is correlated with the iris image data that was captured at the same time that the biomechanical data was measured. Thus, each point of biomechanical data can be correlated with the respective iris image data that was obtained at the measurement time associated with that point of biomechanical data.

At step 420, the corneal tomography data is correlated with the iris image data that was captured at the same time that the corneal tomography data was measured. This can be achieved by correlating the tomography data to the iris image data based on the time data associated with each data set.

Accordingly, after step 418 and step 420, the biomechanical data and the corneal tomography data can be cross-referenced against a common frame of reference provided by the iris image data associated with both the biomechanical data and the corneal tomography data. At step 422, the 3D voxel data is generated by correlating the biomechanical data with the corneal tomography data based on the respectively associated iris image data. The 3D voxel data thus provides a three dimensional mapping of the biomechanical data, the corneal tomography data, and the iris image data.

At step 424, the 3D voxel data can be utilized to develop a treatment plan. The treatment plan is thus, in part, based on the iris image data, which can be subsequently utilized during an eye therapy procedure to ensure that the treatment plan is precisely applied to the eye 1 despite movement of the eye 1.

At step 426, the treatment plan is programmed into an eye treatment system. At step 428, the eye treatment system applies an eye therapy according to the treatment plan. For example, the eye treatment system can include a cross-linking system, a LASIK system, a thermokeratoplasty system, combinations thereof, and/or the like. One non-limiting example of a suitable cross-linking system is the PIXL system manufactured by AVEDRO, Inc. (Waltham, Mass.). The eye treatment system includes an eye tracking system that is configured to monitor the patient's iris. As described above, the application of the eye therapy can include tracking the iris to automatically apply the eye therapy in proper orientation and alignment with the treatment plan (based on the iris image data aspects of the 3D voxel data underlying the treatment plan).

FIG. 5, described by way of example above, represents one algorithm that corresponds to at least some instructions executed by the processor(s) 5 to perform the above described functions associated with the described concepts. It is also within the scope and spirit of the present concepts to omit steps, include additional steps, and/or modify the order of steps presented above. Additionally, it is contemplated that one or more of the steps presented above can be performed simultaneously.

According to some aspects of the present invention, the 3D voxel data can be determined prior to any eye treatment therapy being applied to the eye 1. In such instances, the 3D voxel data can be utilized to diagnose particular eye conditions of the eye 1. Additionally, in such instances, the 3D voxel data can be utilized to determine the treatment plan as described above.

According to additional and/or alternative aspects, the 3D voxel data can be determined during an eye therapy procedure. For example, the 3D voxel data can be utilized to monitor iterative changes to the biomechanical and/or tomographic properties of the eye 1 as the eye therapy is being applied. In some instances, the 3D voxel data can be used as feedback to iteratively determine and/or adjust a treatment plan based on an analysis of the 3D voxel data. In other words, the systems 10, 1010 described and illustrated herein can be employed as a feedback system to iteratively and/or continuously control aspects of the eye therapy being applied to the eye 1.

It is contemplated that the feedback provided by the systems and methods of the present invention can be utilized to determine when milestones are achieved during an eye therapy procedure. For example, during a cross-linking procedure, a first pattern of photoactivating light can be applied until the processor(s) 5 determines that the 3D voxel data is indicative of a first shape change (i.e., a first milestone), then a second pattern can be applied until the processor(s) 5 determines that the 3D voxel data is indicative of a second shape change, and so on. It should be understand that other eye therapy procedure parameters can be similarly controlled based on the 3D voxel data determined and processed as feedback by the systems and methods of the present invention.

According to other additional and/or alternative aspects, the 3D voxel data can be determined after an eye therapy procedure. For example, the 3D voxel data can be utilized to verify whether the eye therapy achieved the intended result. As another example, the 3D voxel data can be utilized to comparatively analyze the post-operative conditions of the eye 1 relative to the pre-operative conditions. Additionally, for example, the 3D voxel data can be utilized to monitor the conditions of the eye 1 to ensure that the changes effected by the eye therapy are stable. In particular, the 3D voxel data can be determined and analyzed after a cross-linking eye therapy procedure to confirm that the strengthening of the corneal tissue is stable and/or identify potential issues with the stability of the corneal tissue strengthening.

While the method 400 is described and illustrated with respect to iris imaging and iris image data, it should be understood that the method 400 can additionally and/or alternatively include the other types of registration imaging and resulting registration data described above. Accordingly, the registration aspects of the systems 10, 1010 and methods 400 can include imaging of one or more anatomical features (e.g., one or more iris textures, scleral arteries, scleral veins, retinal arteries, retinal veins, limbus boundary, scleral boundary, etc.) and/or one or more external information (e.g., structured light) according to some aspects of the present invention.

In the example system 10 illustrated and described above with respect to FIGS. 1 and 3, the spectrometer 300 measures the scattered light received from the CSM head 200, 200' with a VIPA 305 and a line scan camera 315, which can employ an electron multiplying charge-coupled device (EM-CCD) camera. While a EMCCD camera is a highly sensitive sensor that is well suited for Brillouin imaging, EMCCD cameras are sensitive over a broad range of wavelengths that are not needed for Brillouin microscopy. It has been discovered that another approach can provide improved response times and a lower cost compared to EMCCD cameras. In particular, it has been discovered that a photomultiplier (PMT) can be utilized instead of the VIPA and line scan camera employed in the system 10 described above.

Figure 6:
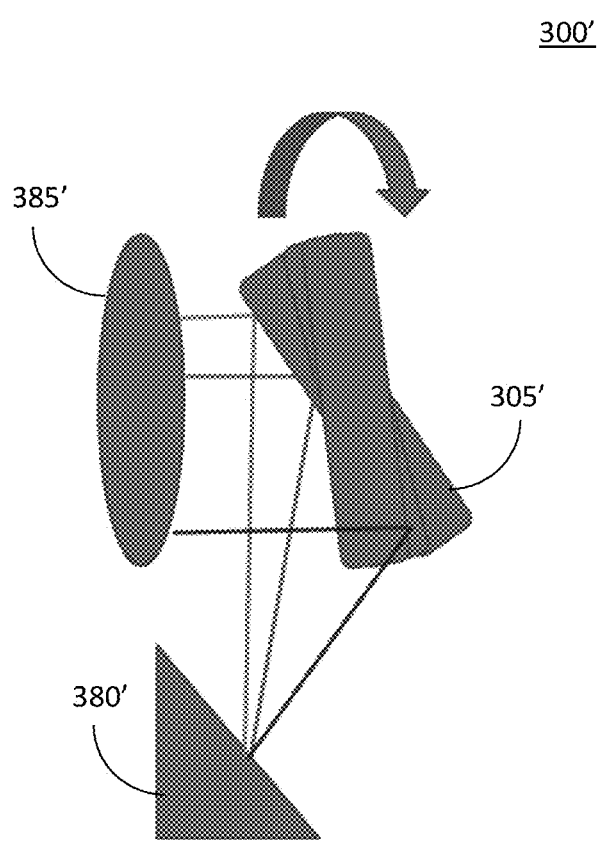
FIG. 6 is a schematic diagram of an example spectrometer according to some aspects of the present invention.

FIG. 6 illustrates aspects of an alternative example spectrometer 300', which can be used with the system 10. The spectrometer 300' includes a PMT 380' with a narrow entrance slit. In the illustrated example, the PMT 380' is stationary while the light beam to be analyzed is scanned from an imaging lens 385' across a face of the PMT 380'. More particularly, a scanning mechanism 305' (e.g., a galvo scanner, polygonal scanner, etc.) can be placed after the imaging lens 385' to direct the light from the imaging lens 385' such that it focuses on the PMT 380'. A slit of pre-calculated width is placed on the PMT entrance. As the scanning mechanism 305' actuates, different peaks of the incident light signal are scanned across the entrance slit.

According to some non-limiting examples, a galvo scanner can be employed as the scanning mechanism 305' with a scan rate as fast as approximately 14 kHz. Typical rise times of the PMT 380' can be of the order of 30 ns. Thus, in such examples, the PMT 380' can provide a readout of about 2380 points per sweep. Accordingly, the galvo scanner and PMT 380' provide sufficient resolution to measure and calculate the Brillouin shift. It is contemplated that the data rates may be increased further by using a polygonal scanner (which may have a scan rate of approximately 25 kHz).

Additionally, it has been found that a PMT 380' based spectrometer 300' such as the example illustrated in FIG. 6 can also enhance the signal-to-noise ratio (e.g., by using a boxcar integrator). In particular, by recording multiple sweeps at the same spatial location on the eye 1 and using a boxcar integrator, the signal-to-noise ratio can be increased.

While the PMT 380' based spectrometer 300' is described above employs a scanning mechanism 305' to scan the light over the face of the PMT 380', it is contemplated that, according to alternative aspects of the present invention, the PMT 380' can be scanned spatially to acquire the Brillouin signal spread along a line.

The embodiments above propose various configurations for a spectrometer system for separating the frequencies of light scattered by an into the Brillouin, Rayleigh, and Raman peaks. It is understood that aspects of the present invention may employ a spectrometer system that uses any appropriate technique. In general, the spectrometer system may use a VIPA, interferometer, grating, or grazing incidence grating, which may be used in combination with a line scan camera with either physical or narrow bandwidth filters. These images may then be reconstructed to achieve the three dimensional mapping as described further above.

Although the example systems and methods described herein may be directed to measuring biomechanical properties of the eye to plan, implement, and assess treatments of the eye, it is contemplated that aspects of the present invention may apply to analysis involving other body parts. For example, aspects of the system 1010 described above may be employed in the field of cardiology where the cardio-vasculature is imaged. In such an application, the system may include a sample arm fiber that is coupled to a rotating fiber that is placed down a catheter. A 360 degree image of the lumen of the vessel is obtained. The fiber is then slowly withdrawn to obtain a 3D mapping of the vessel.

The present disclosure includes systems having processors (sometimes considered controllers) for providing various functionality to process information and determine results based on inputs. Generally, the processors (such as the processors 5 described throughout the present disclosure and illustrated in the figures) may be implemented as a combination of hardware and software elements. The hardware aspects may include combinations of operatively coupled hardware components including microprocessors, logical circuitry, communication/networking ports, digital filters, memory, or logical circuitry. The processor may be adapted to perform operations specified by a computer-executable code, which may be stored on a computer readable medium. The processors 5 may be implemented in any device, system, or subsystem to provide functionality and operation according to aspects of the present invention.

The processor(s) 5 may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), microcontrollers, and the like, programmed according to the teachings of the example embodiments of the present disclosure, as is appreciated by those skilled in the computer and software arts. The physical processors and/or machines may be externally networked with image capture device(s) (e.g., the image capture device 265'), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the example embodiments of the present disclosure may include software for controlling the devices and subsystems of the exemplary embodiments, for driving the devices and subsystems of the example embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

The processor(s) 5 may include, or be otherwise combined with, computer-readable media 6. Some forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the systems and methods of the present invention are described above and illustrated as being directed to measuring biomechanical properties and tomography information for a cornea, it should be understood that the systems and methods of the present invention can also be employed for other target features of the eye. For example, the systems and methods of the present invention can be additionally and/or alternatively employed to plan, implement, and assess treatments for an intraocular lens and/or a retina of the eye. Accordingly, the biomechanical data can be based on the Brillouin scattering measurements of the cornea, the intraocular lens and/or the retina, and the corneal tomography data can be more generally characterized as tomography data measured for the cornea, the intraocular lens, and/or the retina. It should thus be understood that the biomechanical data and the tomography data for the intraocular lens and/or the retina can be correlated based on the registration data to develop, implement, and/or assess treatment plans for the intraocular lens and/or the retina as described above for the corneal implementations of the present invention.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

We claim:

1. A system for measuring biomechanical properties of the eye to at least one of plan, implement, or assess treatments of the eye, the system comprising:
 a biomechanical measurement system, including:
  a light source configured to provide an incident light,
  a confocal microscopy system configured to direct the incident light at a plurality of sections of a target feature of the eye, the incident light being scattered by the plurality of sections of the target feature of the eye, and
  a spectrometer configured to receive the scattered light and process frequency characteristics of the received scattered light to measure a Brillouin frequency shift in the scattered light, the biomechanical measurement system being configured to determine biomechanical data based on the measured Brillouin frequency shift;
 a tomography measurement system configured to measure a tomography of the target feature of the eye and generate tomographic data indicative of the measured tomography;
 a registration system configured to determine registration data relating to one or more anatomical features;
 one or more processors communicatively coupled to the biomechanical system, the tomography system, and the registration system, the one or more processors including a processor clock; and
 one or more memory devices storing instructions that, when executed by the one or more processors, cause the one or more processors to:
  generate time stamp data, based on the processor clock, for each of the biomechanical data, the tomographic data, and the registration data;
  store the biomechanical data with the associated time stamp data in the one or more memory devices;
  store the tomographic data with the associated time stamp data in the one or more memory devices;
  store the registration data with the associated time stamp data in the one or more memory devices;
  for each of the biomechanical data, determine which of the registration data has the same associated time stamp data;
  for each of the tomographic data, determine which of the registration data has the same associated time stamp data; and
  generate three-dimensional voxel data by correlating each of the biomechanical data with each of the tomographic data determined to have the same associated registration data, each of the three-dimensional voxel data including an indication of at least one of the biomechanical data, at least one of the tomographic data, and at least one of the registration data.

2. The system according to claim 1, wherein the tomography measurement system includes a plurality of stereoscopic cameras.

3. The system according to claim 1, wherein the registration system is configured to image the one or more anatomical features of the eye and the registration data is indicative of the imaged one or more anatomical features of the eye.

4. The system according to claim 1, wherein one or more components of each of the biomechanical measurement system, the tomography measurement system, and the registration system are located in a single confocal microscopy scan head.

5. The system according to claim 1, wherein the instructions, when executed by the one or more processors, further cause the one or more processors to determine a treatment plan based on the three-dimensional voxel data.

6. The system according to claim 1, wherein the registration system comprises:
 a registration-light source configured to provide a structured light to create a pattern on the eye; and an imaging system configured to image the pattern on the eye, the imaging system being configured to determine the registration data indicative of a position and an orientation of the eye.

7. The system according to claim 1, wherein the scattered light includes one or more Brillouin-scattered light frequencies and a Rayleigh-scattered light frequency, the biomechanical measurement system further including a virtual image phased array (VIPA) that is configured to separate Rayleigh-scattered light frequency from the one or more Brillouin-scattered light frequencies and a line scan camera configured to measure the scattered light from the VIPA.

8. The system according to claim 1, wherein the spectrometer includes scanning mechanism and a photomultiplier (PMT), the PMT having a narrow entrance slit, the scanning mechanism being configured to scan the scattered light across a face of the PMT such that a plurality of different peaks of the scattered light are scanned across the entrance slit of the PMT.

9. The system of claim 1, wherein the biomechanical measurement system further includes a filter or attenuating device configured to block or attenuate a Rayleigh peak frequency of the scattered light.

10. The system according to claim 1, wherein the biomechanical measurement system includes an optical fiber, a modulated fiber Bragg grating (FBG), and a radio frequency source, the scattered light being directed from the confocal microscopy system to the spectrometer via the optical fiber, the radio frequency source being configured to modulate the FBG to identify Brillouin or Raman frequencies in the scattered light.

11. The system according to claim 1, wherein the target feature of the eye is a cornea.

12. The system according to claim 1, wherein the target feature of the eye is an intraocular lens.

13. The system of claim 3, wherein the one or more anatomical features include an iris of the eye.

14. The system of claim 3, wherein the one or more anatomical features includes at least one of a scleral artery, a scleral vein, a retinal artery, a retinal vein, or a scleral boundary.

15. The system according to claim 5, further comprising an eye treatment system configured to apply an eye treatment to the eye, the eye treatment system including an eye tracking device configured to monitor the one or more anatomical features of the eye, the eye treatment system being configured to be automatically oriented and aligned relative to eye based on the treatment plan and the monitoring of the one or more anatomical features of the eye by the eye tracking device.

16. The system according to claim 15, wherein the instructions, when executed by the one or more processors, cause the one or more processors to determine additional three-dimensional voxel data during eye treatment based on the treatment plan.

17. The system according to claim 15, wherein the instructions, when executed by the one or more processors, cause the one or more processors to determine additional three-dimensional voxel data after the eye treatment based on the treatment plan.

18. The system according to claim 16, wherein the instructions, when executed by the one or more processors, cause the one or more processors to iteratively adjust the treatment plan based on the additional three-dimensional voxel data.

19. The system according to claim 9, wherein the filter or attenuating device includes a Rubidium vapor cell tuned to block the Rayleigh peak frequency.

20. The system according to claim 10, wherein the beat frequency identifies a Stokes Brillouin peak and an Anti-Stokes Brillouin peak, the Brillouin frequency shift being determined from the Stokes Brillouin peak and an Anti-Stokes Brillouin peak.

21. A method for measuring biomechanical properties of the eye to at least one of plan, implement, or assess treatments of the eye, the method comprising:
    directing an incident light from a light source, via a confocal microscopy system, at a plurality of sections of a target feature of the eye, the incident light being scattered by the plurality of sections of the target feature of the eye;
    receiving the scattered light in a spectrometer;
    processing frequency characteristics of the received scattered light to measure a Brillouin frequency shift in the scattered light;
    determining biomechanical data based on the measured Brillouin frequency shift; measuring a tomography of the target feature of the eye;
    determining tomographic data indicative of the measured tomography;
    determining registration data relating to one or more anatomical features;
    determining, based on a processor clock provided by one or more processors, time stamp data for each of the biomechanical data, the tomographic data, and the registration data;
    storing the biomechanical data with the associated time stamp data in one or more memory devices;
    storing the tomographic data with the associated time stamp data in the one or more memory devices;
    storing the registration data with the associated time stamp data in the one or more memory devices;
    for each of the biomechanical data, determining which of the registration data has the same associated time stamp data;
    for each of the tomographic data, determining which of the registration data has the same associated time stamp data; and
    determining three-dimensional voxel data by correlating each of the biomechanical data with each of the tomographic data determined to have the same associated registration data, each of the three-dimensional voxel data including an indication of at least one of the biomechanical data, at least one of the tomographic data, and at least one of the registration data.

22. The method according to claim 21, wherein the registration data is determined from images of the one or more anatomical features and the one or more anatomical features include an iris of the eye.

23. The method according to claim 21, wherein the registration data is determined from images of the one or more anatomical features and the one or more anatomical features include at least one of a scleral artery, a scleral vein, a retinal artery, a retinal vein, or a scleral boundary.

24. The method according to claim 21, wherein the registration data determined from structured light applied to the eye.

25. The method according to claim 21, further comprising determining a treatment plan based on the three-dimensional voxel data.

26. The method according to claim 21, wherein the target feature of the eye is a cornea.

27. The method according to claim 21, wherein the target feature of the eye is an intraocular lens.

28. The method according to claim 25, further comprising:
   applying an eye treatment based on the treatment plan to the eye with an eye treatment system, the eye treatment system including an eye tracking device configured to monitor the one or more anatomical feature of the eye,
   monitoring the one or more anatomical feature of the eye using the eye tracking device; and
   automatically orienting and aligning the application of the eye treatment relative to eye based on the treatment plan and the monitoring of the one or more anatomical features by the eye tracking device.

29. The method according to claim 28, further comprising: determining additional three-dimensional voxel data during the application of the eye treatment based on the treatment plan; and iteratively adjust the treatment plan based on the additional three-dimensional voxel data.

30. The method according to claim 29, further comprising determining additional three-dimensional voxel data after the application of the eye treatment based on the treatment plan.

\* \* \* \* \*